United States Patent [19]

Ranken et al.

[11] Patent Number: 4,760,188

[45] Date of Patent: Jul. 26, 1988

[54] SUBSTITUTED DIAMINOTOLUENE

[75] Inventors: Paul F. Ranken, Baton Rouge, La.; Bonnie G. McKinnie, Magnolia, Ark.

[73] Assignee: Ethyl Corporation, Richmond, Va.

[21] Appl. No.: 917,168

[22] Filed: Oct. 9, 1986

Related U.S. Application Data

[60] Continuation-in-part of Ser. No. 783,421, Oct. 3, 1985, abandoned, which is a division of Ser. No. 619,675, Jun. 11, 1984, Pat. No. 4,594,453.

[51] Int. Cl.$^4$ .......................................... C07C 149/42
[52] U.S. Cl. .................................................... 564/440
[58] Field of Search ........................................ 564/440

[56] References Cited

U.S. PATENT DOCUMENTS

| | | | |
|---|---|---|---|
| 1,940,757 | 12/1933 | Lehmann et al. | 564/440 |
| 4,146,688 | 3/1979 | Schwindt et al. | 521/159 |
| 4,594,453 | 6/1986 | Ranken et al. | 564/440 |
| 4,595,742 | 6/1986 | Nalepa et al. | 528/64 |

OTHER PUBLICATIONS

Pullin et al., *Journal of the American College of Toxicology*, vol. 4, No. 6, 1985, p. 109.

*Primary Examiner*—Glennon H. Hollrah
*Assistant Examiner*—John A. Sopp
*Attorney, Agent, or Firm*—Patricia J. Hogan

[57] ABSTRACT 3,5-Di(methylthio)-2,4-diaminotoluene is a novel compound which is particularly useful as a chain extender in the preparation of polyurethanes.

1 Claim, No Drawings

SUBSTITUTED DIAMINOTOLUENE

CROSS-REFERENCE TO RELATED APPLICATION

This application is a continuation-in-part of copending application Ser. No. 783,421, filed Oct. 3, 1985, now abandoned, which in turn is a division of Ser. No. 619,675, filed June 11, 1984, now U.S. Pat. No. 4,594,453.

BACKGROUND

As disclosed in U.S. Pat. No. 4,146,688 (Schwindt et al.), it is known that aromatic diamines can be used as chain extenders in the preparation of polyurethanes. However, some aromatic diamines are too reactive with isocyanates to permit proper handling, and it has also been found that some aromatic diamines provide polyurethanes having unsatisfactory physical properties. Another problem apt to be presented by the use of aromatic diamines is that many such compounds are known to be toxic or have a structure such as to make it predictable that, when tested, they will probably prove to be carcinogenic.

SUMMARY OF THE INVENTION

An object of this invention is to provide a novel aromatic diamine.

Another object is to provide a novel aromatic diamine which is suitable for the preparation of polyurethanes having acceptable physical properties.

A further object is to provide such an aromatic diamine which lacks the toxicological problems of carcinogenic diamines.

These and other objects are attained by the provision of 3,5-di(methylthio)-2,4-diaminotoluene.

DETAILED DESCRIPTION

The substituted diaminotoluene of the invention can be prepared by reacting 2,4-diaminotoluene with methyl disulfide in the presence of a suitable catalyst, such as aluminum chloride, cuprous iodide, etc., at a temperature in the range of about 20°–300° C. The 2,4-diaminotoluene used in the reaction may be pure or crude, and it is frequently desirable to employ a commercial mixture of 80% 2,4-diaminotoluene and 20% 2,6-diaminotoluene as the starting material. The methyl disulfide is generally employed in at least the stoichiometric amount, although at least some desired product can be obtained when a lesser amount of methyl disulfide is used. The amount of catalyst utilized is a catalytic amount, generally an amount such as to provide a catalyst/diaminotoluene mol ratio of about 0.01-0.5/1, as taught more fully in U.S. Pat. No. 4,594,453 (Ranken et al.), the teachings of which are incorporated herein in toto by reference.

The 3,5-di(methylthio)-2,4-diaminotoluene formed by the reaction is particularly useful as a chain extender in the preparation of polyurethanes. As taught in U.S. Pat. No. 4,595,742 (Nalepa et al.), the teachings of which are incorporated herein in toto by reference, the compound can be effectively employed for this use without having to be separated from other products of the reaction; and its utilization provides for a suitable pot life and leads to the formation of polyurethanes having acceptable physical properties. The compound also has the advantage of being toxicologically acceptable.

The following example is given to illustrate the invention and is not intended as a limitation thereof.

EXAMPLE

A mixture of 0.2 mol of 2,4-diaminotoluene and 0.013 mol of aluminum chloride was stirred at 150° C. in a nitrogen atmosphere for 30 minutes and cooled to 100° C. Then 0.3 mol of methyl disulfide was added, and the reaction mixture was stirred at reflux to a pot temperature of 150° C. in about 20 hours. The reaction mixture was cooled, diluted with 100 ml of ether, and treated with 50 ml of 1N NaOH and then with 50 ml of saturated aqueous NaCl. The combined aqueous portions were treated with 25 ml of ether, and the solvent was removed from the combined organic portions under reduced pressure (40 mm) with a rotary evaporator to give 32.6 g of crude product. Analysis by gas chromatography showed 13 area % 2,4-diaminotoluene, 12 area % 3-(methylthio)-2,4-diaminotoluene, 45 area % 5-(methylthio)-2,4-diaminotoluene, and 31 area % 3,5-di(methylthio)-2,4-diaminotoluene.

What is claimed is:

1. 3,5-Di(methylthio)-2,4-diaminotoluene.

* * * * *